(12) United States Patent
Iwahara

(10) Patent No.: US 6,586,637 B2
(45) Date of Patent: Jul. 1, 2003

(54) PROCESS FOR PRODUCING BISPHENOL A

(75) Inventor: Masahiro Iwahara, Yamaguchi (JP)

(73) Assignee: Idemitsu Petrochemical Co., Ltd., Tokyo (JP)

(*) Notice: Subject to any disclaimer, the term of this patent is extended or adjusted under 35 U.S.C. 154(b) by 0 days.

(21) Appl. No.: 09/926,131

(22) PCT Filed: Jan. 17, 2001

(86) PCT No.: PCT/JP01/00257
§ 371 (c)(1),
(2), (4) Date: Sep. 7, 2001

(87) PCT Pub. No.: WO01/53238
PCT Pub. Date: Jul. 26, 2001

(65) Prior Publication Data
US 2003/0013925 A1 Jan. 16, 2003

(30) Foreign Application Priority Data
Jan. 18, 2000 (JP) ....................................... 2000-008562

(51) Int. Cl.$^7$ .............................................. C07C 39/16
(52) U.S. Cl. ..................................................... 568/728
(58) Field of Search ................................. 568/727, 728

(56) References Cited

U.S. PATENT DOCUMENTS

| 4,051,079 | A | * | 9/1977 | Melby |
| 5,399,784 | A | * | 3/1995 | Asaoka |
| 5,502,016 | A | * | 3/1996 | Kiedik |

FOREIGN PATENT DOCUMENTS

| JP | 06-107579 | 4/1994 |
| JP | 08-325185 | 12/1996 |
| JP | 09-176069 | 7/1997 |
| JP | 2000-143565 | 5/2000 |

* cited by examiner

*Primary Examiner*—Michael L. Shippen
(74) *Attorney, Agent, or Firm*—Oblon, Spivak, McClelland, Maier & Neustadt, P.C.

(57) ABSTRACT

Acetone and phenol are reacted in the presence of an acid-type ion exchange resin. The reaction mixture obtained from the reaction is subjected to a reduced-pressure distillation to recover bisphenol A as a fraction discharged from the bottom of a distillation column. Before the reaction, the acid-type ion exchange resin is washed with phenol to produce a phenol solution. The phenol solution is distilled together with a fraction obtained from the top of a distillation column. The bisphenol A produced in the process exhibits a stable hue.

20 Claims, No Drawings

PROCESS FOR PRODUCING BISPHENOL A

BACKGROUND OF THE INVENTION

1. Field of the Invention

The present invention relates to a process for producing bisphenol A exhibiting a stable hue. The thus produced bisphenol A is useful as raw materials of polycarbonate resins, epoxy resins, polyarylate resins or the like.

2. Background Arts

As well known in the arts, bisphenol A [2,2-bis(4-hydroxyphenyl) propane] is an important compound useful as raw material of engineering plastics such as polycarbonate resins and polyarylate resins, or epoxy resins. Recently, the demand for the above compound tends to be more and more increased. In particular, when used as raw material of polycarbonate resins, the bisphenol A has been required to exhibit a stable hue without undesired coloration even when it is treated at an elevated temperature.

It is also known that the bisphenol A is produced by condensing phenol with acetone in the presence of an acid-type ion exchange resin as a catalyst. In this case, the acid-type ion exchange resin is usually swelled with water and packed in a reactor. After packing, the ion exchange resin is washed with water to remove acid substances therefrom, and then washed with phenol prior to its use in the reaction. Conventionally, the phenol used for the washing has been usually mixed with a reaction mixture discharged from outlet of the reactor in order to recover and purify the phenol. For this reason, the thus produced bisphenol A inevitably contains acid substances, resulting in deteriorated hue thereof.

DISCLOSURE OF THE INVENTION

The present invention has been made in view of the above problems. An object of the present invention is to provide a process for producing bisphenol A exhibiting a stable hue without undesired coloration even when treated at an elevated temperature.

As the result of extensive studies, the present inventors have found that the above object is achieved by removing acid substances from a phenol solution obtained after washing the acid-type ion exchange resin. The present invention has been accomplished based on this finding.

Thus, the present invention provides a process for producing bisphenol A by reacting acetone with phenol in the presence of an acid-type ion exchange resin as a catalyst and then subjecting the reaction mixture to a reduced-pressure distillation to recover the bisphenol A from a fraction discharged from a bottom of distillation column, comprising:

washing said acid-type ion exchange resin filled in a reactor with phenol before using the ion exchange resin in the reaction; and distilling a phenol solution obtained after the washing together with a fraction obtained from a top of the distillation column for recovery of phenol.

DESCRIPTION OF THE PREFERRED EMBODIMENTS

The present invention will be described in detail below.

First, the respective steps of the process for the production of bisphenol A is described.

Step (1): Reaction Step

Bisphenol A is produced by reacting acetone with an excess amount of phenol in the presence of an acid-type ion exchange resin as catalyst and, if required, alkylmercaptan as co-catalyst. As the suitable acid-type ion exchange resin as catalyst, there may be generally used sulfonic acid-type cation exchange resins. Examples of such sulfonic acid-type cation exchange resins include sulfonated styrene divinyl benzene copolymers, sulfonated cross-linked styrene polymers, phenol formaldehyde-sulfonic acid resins, benzene formaldehyde-sulfonic acid resins or the like. These sulfonic acid-type cation exchange resins may be used alone or in the form of a mixture of any two or more thereof.

The suitable alkylmercaptan used as co-catalyst are such mercaptans having a $C_1$–$C_{10}$ alkyl group. Examples of the alkylmercaptans include methylmercaptan, ethylmercaptan, propylmercaptan, octylmercaptan, cyclohexylmercaptan or the like. Among these alkylmercaptans, ethylmercaptan is especially preferred. Meanwhile, these alkylmercaptans may be used alone or in the form of a mixture of any two or more thereof.

The above reaction may be desirably conducted by a fixed-bed continuous or batch method, though not limited thereto. When the reaction is conducted by fixed-bed continuous method, the liquid hourly space velocity (LHSV) used therein is usually in the range of 0.2 to 30 $Hr^{-1}$, preferably 0.5 to 6 $Hr^{-1}$.

As to the other reaction conditions, the reaction temperature is 60 to 100° C.; the molar ratio of phenol to acetone is 6 to 13; and the molar ratio of acetone to mercaptan is 13 to 25.

The resultant reaction mixture contains, in addition to bisphenol A, unreacted phenol, unreacted acetone, catalysts, by-produced water, alkylmercaptan, and other by-products such as organic sulfur compounds and colored substances.

Step (2): Recovery of By-Produced Water and Unreacted Raw Materials

Then, the reaction mixture obtained in the step (1) is distilled under reduced pressure to remove unreacted acetone, by-produced water, alkylmercaptan, a part of unreacted phenol and the like from a top of distillation column and obtain a liquid mixture containing bisphenol A, phenol, etc., from the bottom thereof. The reduced-pressure distillation may be conducted at a temperature of 70 to 180° C. under a pressure of 6.7 to 80.0 kPa. Upon such a distillation, the unreacted phenol is subjected to azeotropy, and removed out of the reaction system from the top of the distillation column.

Step (3): Concentration of Bisphenol A

The bottoms obtained by removing the above substances from the reaction mixture, is then distilled under reduced pressure to remove unreacted phenol therefrom and concentrate bisphenol A contained therein. The thus obtained concentrated residual solution is used as a raw material of the subsequent crystallization step. The concentration conditions are not particularly restricted, but the concentration process may be usually conducted at a temperature of 100 to 170° C. under a pressure of 5.3 to 66.7 kPa. When the temperature is less than 100° C., it is necessary to keep the reaction system under high vacuum condition. On the contrary, when the temperature is more than 170° C., an additional heat-removal step is required upon conducting the subsequent crystallization step. The concentration of bisphenol A contained in the concentrated residual solution is in the range of 20 to 50% by weight, preferably 20 to 40% by weight. When the concentration of bisphenol A contained in the concentrated residual solution is less than 20% by weight, the recovery percentage of bisphenol A becomes lowered. On the contrary, when the concentration of bisphenol A in the residual solution is more than 50% by weight, it is difficult to transport a slurry obtained after the crystallization step.

Step (4): Crystallization

The concentrated residual solution obtained in the step (3) is cooled to a temperature of 40 to 70° C. to crystallize an adduct of bisphenol A and phenol (hereinafter referred to merely as "phenol adduct"), thereby obtaining a slurry. The cooling is conducted due to heat removal caused by evaporating water added to external heat exchanger and crystallizer. Next, the slurry-like concentrated residual solution is subjected to filtration, centrifugal separation, etc., and separated into the phenol adduct and a crystallization mother liquor containing by-products. The thus obtained crystallization mother liquor may be directly or partially recycled to the reactor, or recovered in the form of phenol and isopropenyl phenol by subjecting whole or part thereof to alkali decomposition. Alternatively, a part or whole of the crystallization mother liquor may be isomerized and recycled as raw material to the crystallization step (refer to Japanese Patent Laid-open No. 6-321834).

Step (5): Heat-Melting of Phenol Adduct

The 1:1 adduct of bisphenol A and phenol obtained in the step (4) in the form of crystals, is heat-melted at a temperature of 100 to 160° C. to obtain a liquid mixture.

Step (6): Recovery of Bisphenol A

The liquid mixture obtained in the step (5) is distilled under reduced pressure to remove phenol and recover bisphenol A therefrom. The reduced-pressure distillation is conducted at a temperature of 150 to 190° C. under a pressure of 1.3 to 13.3 kPa. In addition, the removal of residual phenol may be conducted by known methods such as steam-stripping.

Step (7): Granulation of Bispherol A

The molten bisphenol A obtained in the step (6) is formed into droplets using a granulating apparatus such as spray dryer, and cooled and solidified to obtain an aimed product. The droplets are produced by spraying, spreading or the like method, and cooled with nitrogen, air or the like.

In the present invention, the acid-type ion exchange resin filled in the reactor is washed with phenol before used in the reaction, and a phenol solution obtained after the washing (hereinafter referred to merely as a "washing phenol solution") is distilled together with a fraction (containing acetone, by-produced water, phenol and alkylmercaptan) obtained from a top of the reduced-pressure distillation column used in the above step (2) to recover phenol therefrom and recycle the recovered phenol. In the distillation, only one distillation column may be used to separate the mixture into respective components by varying the distillation conditions. Alternatively, several distillation columns may be used to separate the mixture into respective components. The washing phenol solution and the fraction obtained from the top of the above reduced-pressure distillation column may be continuously or intermittently mixed together. In any case of the continuous and intermittent mixing methods, the distillation may be conducted in such a manner that the ratio of phenol contained in the washing phenol solution to that recovered from the fraction obtained from the top of the reduced-pressure distillation column is within the range of 1:0.01 to 1:2.

The thus recovered phenol contains no acid substances and is therefore reusable as the raw material.

Meanwhile, the washing phenol solution may be temporarily stored before use.

Next, the process of the present invention will be described in more detail below. However, these examples are only illustrative and not intended to limit the present invention thereto.

EXAMPLE 1

A packed bed-type reactor having an inner diameter of 13 mm and a height of 560 mm was filled with 74 cc of a water-swelled sulfonic acid-type cation exchange resin ("DIAION-104H" available from Mitsubishi Chemical Corp.). While maintaining the reaction temperature at 60° C., the sulfonic acid-type cation exchange resin filled in the reactor was washed with 80 cc of water and then with 110 cc of phenol. The resultant solution obtained after washing the ion exchange resin with phenol was recovered in a flask. It was confirmed that the recovered washing phenol solution contained about 49% by weight of water and 3 weight ppm of sulfonic acid (in terms of p-toluenesulfonic acid).

The washing phenol solution was heated under ordinary pressure to remove water therefrom, and then treated at 170° C. under reduced pressure to recover phenol therefrom and purify the recovered phenol. As a result, it was confirmed that the thus purified phenol contained about 1,000 weight ppm of water, but did not contain any sulfonic acid.

After completion of washing the above catalyst, phenol, acetone and ethylmercaptan were fed from an inlet of the reactor and passed therethrough at a liquid hourly space velocity (LHSV) of 1 $Hr^{-1}$ in such amounts that the molar ratio of phenol to acetone was 10 and the molar ratio of acetone to ethylmercaptan was 20, thereby conducting the reaction at 80° C. (acetone conversion rate: 75%).

The purification and hue of the reaction solution was evaluated by the following method.

The reaction solution was distilled at 170° C. under reduced pressure to remove unreacted acetone, by-produced water, ethylmercaptan and a part of unreacted phenol therefrom. The remaining solution was further distilled at 154° C. under reduced pressure to remove an excess amount of phenol therefrom and concentrate the bisphenol A contained therein up to 40% by weight. The thus obtained concentrated solution was cooled to 43° C. to crystallize and precipitate an adduct of bisphenol A and phenol, and then subjected to solid-liquid separation The obtained adduct of bisphenol A and phenol in the form of crystals was treated at 170° C.

under a pressure of 4 kPa to remove phenol therefrom and obtain bisphenol A.

The obtained bisphenol A was heated at 175° C. in air for 30 minutes and visually observed using an APHA standard solution to evaluate a hue thereof. As a result, it was confirmed that the hue of the obtained bisphenol A was as good as 10 APHA.

EXAMPLE 2

The same procedure as in EXAMPLE 1 was repeated except that a sulfonic acid-type cation exchange resin ("K1221" available from Bayer A G.) was used. As a result, it was confirmed that the washing phenol solution contained about 49% by weight of water and 7 weight ppm of sulfonic acid (in terms of p-toluenesulfonic acid).

The washing phenol solution was heated under ordinary pressure to remove water therefrom, and then treated at 170° C. under reduced pressure to recover phenol therefrom and purify the recovered phenol. As a result, it was confirmed that the thus purified phenol contained about 950 weight ppm of water, but did not contain any sulfonic acid.

The thus produced bisphenol A exhibited a hue as good as 15 APHA.

COMPARATIVE EXAMPLE 1

The same procedure as in EXAMPLE 1 was repeated except that a mixture of 200 cc of the reaction solution and 20 cc of the phenol solution used for the washing in EXAMPLE 1 was treated to recover and purify bisphenol A As a result, it was confirmed that the thus produced bisphenol A exhibited a hue of 25 APHA.

COMPARATIVE EXAMPLE 2

The same procedure as in EXAMPLE 1 was repeated except that a mixture of 200 cc of the reaction solution and 10 cc of the phenol solution used for the washing in EXAMPLE 2 was treated to recover and purify bisphenol A As a result, it was confirmed that the thus produced bisphenol A exhibited a hue of 30 APHA.

INDUSTRIAL APPLICABILITY

In accordance with the present invention, in the process for producing bisphenol A by reacting acetone with phenol in the presence of an acid-type ion exchange resin as catalyst and then subjecting the reaction mixture to a reduced-pressure distillation to recover the bisphenol A from a fraction discharged from a bottom of distillation column, it is possible to produce bisphenol A exhibiting a stable hue without undesired coloration even when treated at an elevated temperature by washing said acid-type ion exchange resin filled in a reactor with phenol before used in the reaction; and distilling a phenol solution obtained after the washing together with a fraction obtained from a top of the distillation column to recover phenol therefrom.

What is claimed is:

1. A process comprising,
   reacting acetone with phenol in the presence of an acid-type ion exchange resin to form a reaction mixture and then
   subjecting the reaction mixture to a reduced-pressure distillation to recover bisphenol A from a fraction discharged from the bottom of a first distillation column,
   wherein said acid-type ion exchange resin is washed with phenol before the reaction to form a phenol solution; and
   the phenol solution is mixed with a fraction obtained from the top of a second distillation column and distilled to form recovered phenol,
   wherein the first and second distillation columns may be the same or different.

2. The process according to claim 1, wherein the acid-type ion exchange resin is a sulfonic acid-type cation exchange resin.

3. The process according to claim 1, wherein at least one alkylmercaptan is present with the acid-type ion exchange resin.

4. The process according to claim 1, wherein the reaction between phenol and acetone is conducted by a fixed-bed continuous or batch method.

5. The process as claimed in claim 1, wherein the acid-type ion exchange resin is a sulfonic acid-type cation exchange resin selected from the group consisting of sulfonated styrene divinyl benzene copolymers, sulfonated cross-linked styrene polymers, phenol formaldehyde-sulfonic acid resins, benzene-formaldehyde-sulfonic acid resins and mixtures thereof.

6. The process of claim 1, wherein the process is carried out in the presence of at least one alkylmercaptan having a $C_1$–$C_{10}$ alkyl group.

7. The process of claim 1, wherein the reaction is carried out in the presence of an alkylmercaptan selected from the group consisting of methylmercaptan, ethylmercaptan, propylmercaptan, octylmercaptan, cyclohexylmercaptan and mixtures thereof.

8. The process of claim 1, wherein the process is carried out by a fixed-bed continuous method wherein the liquid hourly space velocity is in the range of from 0.2 to 30 $Hr^{-1}$.

9. The process of claim 1, wherein the molar ratio of phenol to acetone is from 6 to 13.

10. The process of claim 1, wherein the reaction mixture is distilled under a pressure of from 6.1 to 80.0 kPa.

11. The process of claim 1, wherein the reaction mixture is distilled at a temperature of from 70 to 180° C.

12. The process of claim 1, further comprising
    concentrating the bisphenol A recovered in a fraction discharged from the bottom of a distillation column to form a concentrated residual solution.

13. The process of claim 12, wherein the fraction discharged from the bottom of a distillation column is concentrated by removing one or more volatile components at a temperature of 110 to 170° C. and a pressure of 5.3 to 66.7 kPa.

14. The process of claim 13, further comprising
    cooling the concentrated residual solution to crystallize an adduct of bisphenol A and phenol.

15. The process of claim 14, further comprising
    melting the adduct to obtain a liquid mixture.

16. The process of claim 15, further comprising distilling the liquid mixture under reduced pressure to recover bisphenol A.

17. The process of claim 16, wherein the liquid mixture is distilled under a pressure of 1.3 to 13.3 kPa.

18. The process of claim 16, wherein the liquid mixture is distilled at a temperature of from 150 to 190° C.

19. The process of claim 16, further comprising granulating the bisphenol A.

20. The process of claim 1, further comprising recycling the recovered phenol to the reaction.

* * * * *